United States Patent
Allison et al.

(10) Patent No.: US 7,122,568 B1
(45) Date of Patent: Oct. 17, 2006

(54) USE OF LOW-DOSE PDT TO INHIBIT RESTENOSIS

(75) Inventors: Beth Anne Allison, Vancouver (CA); Philippe Maria Clotaire Margaron, Burnaby (CA); Valery Rubinchik, Richmond (CA); Russell G. Hodge, Healdsburg, CA (US); Michael David Leslie Stonefield, Vancouver (CA)

(73) Assignee: QLT, Inc., Vancouver (CA)

( * ) Notice: Subject to any disclaimer, the term of this patent is extended or adjusted under 35 U.S.C. 154(b) by 88 days.

(21) Appl. No.: 09/715,478

(22) Filed: Nov. 17, 2000

Related U.S. Application Data
(60) Provisional application No. 60/165,939, filed on Nov. 17, 1999.

(51) Int. Cl.
*A61K 31/40* (2006.01)

(52) U.S. Cl. ....................................................... 514/410
(58) Field of Classification Search .................. 514/410
See application file for complete search history.

(56) References Cited

U.S. PATENT DOCUMENTS

| | | |
|---|---|---|
| 4,883,790 A | 11/1989 | Levy et al. |
| 4,920,143 A | 4/1990 | Levy et al. |
| 5,095,030 A | 3/1992 | Levy et al. |
| 5,171,749 A | 12/1992 | Levy et al. |
| 5,232,444 A | 8/1993 | Just et al. |
| 5,283,255 A | 2/1994 | Levy et al. |
| 5,419,760 A | 5/1995 | Narciso, Jr. |
| 5,422,362 A * | 6/1995 | Vincent et al. ............. 514/410 |
| 5,429,634 A | 7/1995 | Narciso, Jr. |
| 5,458,568 A | 10/1995 | Racchini et al. |
| 5,880,145 A | 3/1999 | Sternberg et al. |
| 5,990,149 A | 11/1999 | Sternberg et al. |
| 6,153,639 A | 11/2000 | Sternberg et al. |

FOREIGN PATENT DOCUMENTS

| | | |
|---|---|---|
| EP | 0906758 A | 4/1999 |
| WO | WO/9211895 | 7/1992 |
| WO | WO/9405361 | 3/1994 |
| WO | WO/9505866 | 3/1995 |
| WO | WO 00/21562 A | 4/2000 |
| WO | WO 01/24825 A | 4/2001 |

OTHER PUBLICATIONS

Coats, W.D. et al. (1996) *Biochem Cell Biol* 74(3):325–331; XP001016394 (abstract; figures 3,4).
Etoh, D. et al. (1995) *Arch Surg* 130(10):1098–1103; XP001024202 (figure 1).
Obochi, M. et al. (1997) *Photochemistry and Photobiology* 65:18S–19S; XP001028504.
Perree, J. et al. (1998) *Proc Spie–Int Soc Opt Eng* 3245:44–50; XP001024173 (abstract).
Harrison's Principle of Internal Medicine, 13h ed., 1994, p. 986, published by McGraw Hill.*
Vincent et al., Progress in biomedical Optics, Proceedings of Laser in surgery: Advanced Characterization, Therapeutics, and Systems VI, 1996, vol. 2671, p. 72–77.*
Adili et al. "Phaotodynamic Therapy wtih Local Photosensitizer Delivery Inhibits Experimental Intimal Hyperplasia" Lasers in Surgery and Medicine 1998, 23: 263–273.*

(Continued)

*Primary Examiner*—San-Ming Hui
(74) *Attorney, Agent, or Firm*—Morrison & Foerster LLP

(57) ABSTRACT

The present invention relates to the use of low-dose photodynamic therapy (PDT) to prevent, treat, inhibit or reduce restenosis in blood vessels. The present invention may be used in combination with any angioplastic procedure to prevent restenosis or to decrease the intima thickness, and thus luminal narrowing.

14 Claims, 1 Drawing Sheet

OTHER PUBLICATIONS

Adili et al. (1999). *Photochemistry and Photobiology.* 70(4):663–668.
Adili et al. (1995). *Lasers in Surgery and Medicine.* 23–263–273.
Adili et al. *SPIE.* 2395:402–408.
Asahara et al. (1992). *Circulation 86 (Suppl).* 1–846.
Eton, D. et al. (1992). *J. Surg. Res.* 53:558–562.
Ferns et al. (2000). *Int. J. Exp. Path.* 81:63–88.
Gonschior et al. (1995). *Amer. Heart J.* 130(6):1174–1181.
Gonschior et al.(1996). *J. Amer. Coll. Cardiol.* 27(2, Suppl A):196A.
Gonschior et al.(1996). *Photochemistry and Photobiology.* 64(5):758–763.
Grant et al. (1994). *Br. J. Cancer.* 70:72–78.
Hsiang et al. (1995). *Ann. Vasc. Surg.* 9:80–86.
Hsiang et al. (1995). *Cardiovasc. Surg.* 3(5):489–494.
Hsiang et al. (1993). *Photobiol.* 53(3):518–525.
Lafont et al. (1998). *Cardiovascular Res.* 39:50–59.
LaMuraglia et al. (1994). *J Vasc Surg.* 19:321–331.
Nyamekye et al. (1996). *Eur. J. Vasc. Endovasc. Surg.* 11:19–28.
Ortu, P. et al. (1992). *Circulation.* 85:1189–1196.
Redmond and Gamlin. (1999). *Photochem. Photobiol.* 70(4):391–475.
Rockson et al. (2000). *Circulation* 102:591–596.
Schwartz (1994). *Lab. Investig.* 71(6):789–791.
Sobeh et al. (1995). *Eur. J. Vasc. Endovasc. Surg.* 9:463–468.
Sobeh et al. (1995). *SPIE* 2395:390–395.

* cited by examiner

USE OF LOW-DOSE PDT TO INHIBIT RESTENOSIS

RELATED APPLICATIONS

The present application claims benefit of priority from U.S. Provisional Patent Application 60/165,939 filed Nov. 17, 1999, which is hereby incorporated by reference in its entirety as if fully set forth. The present application is also related to U.S. patent applications Ser. Nos. 09/169,233, filed Oct. 9, 1998 and 60/129,324, filed Apr. 14, 1999, both of which are hereby incorporated by reference in their entireties, as if fully set forth.

TECHNICAL FIELD

The present invention relates to the use of low-dose photodynamic therapy (PDT) to prevent, treat, inhibit or reduce restenosis, as well as any associated intimal hyperplasia (IH), in blood vessels. The present invention may be used in combination with any angioplastic procedure to prevent restenosis or to decrease the intima thickness, and thus luminal narrowing. The present invention also relates to the modulation, inhibition, or reduction of smooth muscle cell (SMC) growth that is associated with restenosis and any associated IH.

BACKGROUND ART

In humans, angioplasty is an increasingly common invasive vascular procedure whereby luminal narrowing due to increases in intima thickness is reduced by mechanical dilation. One common form of this procedure is where a balloon catheter is expanded at a narrowed site in a blood vessel. Unfortunately, angioplasty often also results in vascular injury which produces subsequent narrowing at the site of angioplasty, referred to as restenosis, as a direct response. The exact causes of restenosis have yet to be completely elucidated, but have been postulated to involve arterial wall remodeling and/or intimal hyperplasia (IH). IH is characterized by cellular proliferation and the accumulation of matrix components on the inner wall of blood vessels, leading to luminal narrowing. IH is also characterized by a thickened fibromuscular layer between the blood vessel's endothelium and the inner elastic lamina (IEL).

Considerable research has aimed at clinical and pharmacological intervention to prevent or treat restenosis, including experimental attempts to use photodynamic therapy (PDT) in animal models. Generally, PDT involves the use of an inert photosensitizer (PS) that is activated by specific wavelength(s) of radiation to produce a toxic agent, thought to be singlet oxygen in the case of porphyrins, which causes the destruction of unwanted cellular tissue. The PS is essentially a catalyst for generating the toxic agent.

Some research has been based upon the observation that PDT may be adapted for photoangioplasty (see Rockson et al. Circulation 102:591–596, 2000) for a recent review. Other research has been based upon the use of PDT to kill smooth muscle cells (SMCs) in vitro (see Sobeh et al. Eur. J. Vasc. Endovasc. Surg. 9:463–468, 1995).

Research with animal models to study the possible use of PDT to prevent or treat human restenosis utilize normal arteries. This is despite the contrasting situation with restenosis in human arteries, which is the response to angioplastic treatment of arteries with pre-existing disease. Such arteries contain advanced atherosclerotic lesions, often with regions of calcification. Treatment of such diseased arteries with angioplastic procedures, such as percutaneous transluminal coronary angioplasty (used as an alternative to coronary artery bypass grafting), frequently results in considerable tissue damage, including tears in the intima and media of the artery. This degree of injury, and thus the subsequent restenotic response, is inadequately modeled in most animal systems used, where simple endothelial denudation, rather than the deeper injury seen with human angioplasty, is used. As such, the results with animal models should be reviewed with caution. For reviews of animal models and restenosis, see Lafont et al. (Cardiovascular Res. 39:50–59, 1998), Ferns et al. (Int. J. Exp. Path. 81:63–88, 2000), and Schwartz (Lab. Investig. 71(6):789, 1994). Interestingly, some of this work has led to the suggestion that arterial remodeling, rather than intimal formation, accounts for restenosis after angioplasty (see Lafont et al.)

One example of PDT in an animal model is described by Asahara et al. (Circulation 86 (Suppl) 1–846, 1992). They observed that PDT was able to inhibit restenosis in rabbits that had been fed a high cholesterol diet and received balloon injuries of the iliac artery. Importantly, they found that immediate PDT treatment following balloon injury was ineffectual at decreasing intimal thickness (expressed as the intima:media, I/M, ratio). Instead, they observed the best results by using PDT one week after balloon injury. Gonschior et al. (Photochemistry and Photobiology, 64(5) :758–763, 1996) conducted similar PDT experiments in a swine model using injury to nondiseased arteries (see also Gonschior et al., J. Amer. Coll. Cardiol. 27(2, Suppl A):196A, 1996).

Other workers have used PDT to inhibit IH and completely deplete endothelial cells, as well as medial cells in some instances, from rat arteries (Nyamekye et al. Eur. J. Vasc. Endovasc. Surg. 11: 19–28, 1996; LaMuraglia et al. Photodynamic therapy inhibition of experimental intimal hyperplasia: acute and chronic effects. J Vasc Surg, 19:321–331, 1994; Grant et al. Br. J. Cancer 70:72–78, 1994; and Ortu, P. et al. Circulation 85:1189–1196, 1992). In all of these instances, the photosensitizer was administered systemically and the radiation performed external to the blood vessel. For example, Ortu et al. used endothelial denudation (with an embolectomy catheter) of normal rat carotid arteries to study PDT with systemically administered chloraluminum-sulfonated phthalocyanine (CASPc) used as the photosensitizing agent. They noted that their denudation protocol did not disrupt the internal elastic lamina (EL) and was effective in inhibiting the induced IH response on day 14 when PDT was conducted on days 2 and 7 after denudation. External irradiation of the artery was used to activate CASPc. It is unknown whether complete depletion as seen in these methods would be safe or advantageous in humans.

Similar depletion of endothelial cells and medial cells were observed by Adili et al. (Lasers in Surgery and Medicine 23:263–273, 1998; and SPIE 2395:402–408, 1995) upon the use of PDT with locally administered photosensitizer in injured rat carotid arteries and 100 J/cm² external photoactivation. In the 1998 work, they reported that the photosensitizer dosage in the vessel wall was approximately 2.5 ng/mg after local pressurized delivery of a 25 µg/ml solution for two minutes and approximately 1.4 ng/mg after systemic delivery of a 2 mg/ml solution via injection. In the 1995 work, they reported similar concentrations of approximately 1.5 ng/mg with both local and systemic administration, at 25 µg/ml and 0.5 mg/kg body weight, respectively. 15 minutes after localized delivery, irradiation was performed externally with 100 $J/cm^2$ of 690 nm light.

Eton, D. et al. (J. Surg. Res. 53:558–562, 1992) used a similar endothelial denudation (with a balloon catheter) of normal rabbit carotid arteries to study PDT with systemically administered Photofrin™. This denudation protocol again leaves the media and adventitia of the artery intact, and PDT was effective in reducing the induced IH response (recorded as a ratio of IH area to normalized area enclosed by the IEL based on cross sectional analysis of the arteries five weeks after PDT). Photofrin™ was systemically administered 7 days after denudation, with external irradiation of the artery two days later. In a similar model, Hsiang et al. (Ann. Vasc. Surg. 9:80–86, 1995) reported the prevention of IH with PDT in rabbit arteries injured by endothelial denudation. In this approach, Photofrin™ was administered systemically after injury, with 120 or 240 J/cm$^2$ irradiation following 24 hours later.

In a porcine model for the prevention of IH, however, Sobeh et al. (SPIE 2395:390–395, 1995) observed the failure of systemic administration of photosensitizer followed by balloon injury and external irradiation to result in the prevention of IH. Instead, they observed that PDT under such conditions resulted in a significant increase of intimal area. The PDT conditions were injection of 0.3 mg/kg of metatetrahydroxyphenyl-chlorin (m-THPC) four hours prior to endothelial denudation and external irradiation with 20 J/cm$^2$ of 652 nm light.

One possible explanation for the above results may be based on the observations of Adili et al. (Photochemistry and Photobiology, 70(4):663–668, 1999) concerning the applied dose of PDT. With the rat carotid artery model, Adili et al. used balloon mediated endothelial denudation before pressurized local delivery of either a 0.5 µg/ml or a 25 µg/ml solution of BPD-MA for two minutes followed 15 minutes later by external irradiation with either 50 or 100 J/cm$^2$ light of 690 nm. The use of 0.5 µg/ml BPD-MA with 50 and 100 J/cm$^2$ light (Stages I and II, respectively) was observed to have little effect on reducing IH. Instead Stage II is noted to be associated with induction of significant IH (see page 666, top of right column). The use of 25 µg/ml BPD-MA with 50 and 100 J/cm$^2$ light (Stages III and IV, respectively) was observed to inhibit IH and induce photothrombosis, respectively. As such, Adili et al. suggest that correct dosimetry is needed to effectively inhibit IH. In particular, relatively low dose PDT is ineffectual while relatively high doses may trigger thrombosis. See Hsiang et al. (Cardiovasc. Surg. 3(5):489–493, 1995, and Photochem. Photobiol. 53(3):518–525, 1993) for previous studies on PS dosages.

Lastly, a variation of PDT, wherein no photoactivation is induced, has also been described as inhibiting restenosis and intimal hyperplasia (see U.S. Pat. No. 5,422,362, which is hereby incorporated by reference in its entirety as if fully set forth).

DISCLOSURE OF THE INVENTION

The present invention provides methods for the efficacious use of low dose photodynamic therapy (PDT) to prevent, treat, inhibit or reduce restenosis and/or intimal hyperplasia (IH) in blood vessels in vivo. Restenosis may follow either a primary or subsequent intervention in a blood vessel, such as secondary, tertiary or further interventions. A non-limiting example of a primary intervention is a procedure used to increase the luminal space, while a non-limiting example of a subsequent intervention is a procedure used to increase the luminal space at a location that has previously undergone a primary intervention.

As such, the methods may be applied to coronary, or peripheral vascular locations at risk of developing de novo restenotic lesions, such as sites of a primary intervention, or vascular containing secondary restenotic lesions, such as "in stent" restenotic lesions. The methods may also be applied to the sites of bypass or other vascular grafts, and may be referred to as photorestenosis therapy, or PRT.

The methods of the invention may be used in combination with an angioplastic procedure used to treat arteriosclerosis, atherosclerosis, or the plaques associated therewith. The administration of the photosensitizer (PS) in the methods of the invention may be performed locally at the site of angioplasty. The administration may occur simultaneously, or roughly simultaneously, with the physical manipulations within a blood vessel during an angioplastic procedure.

After PS administration, the site containing IH or at risk of developing IH is deliberately exposed to radiation containing one or more wavelengths capable of activating said PS. When used in combination with an angioplastic procedure, the irradiation occurs at the site of said procedure. The dosage of PS and irradiation, as well as the duration and frequency of irradiation, are selected to be "low dose" wherein restenosis and/or IH is prevented, treated, inhibited or otherwise reduced in comparison to the absence of such low dose treatment.

MODES OF CARRYING OUT THE INVENTION

Figure 1:
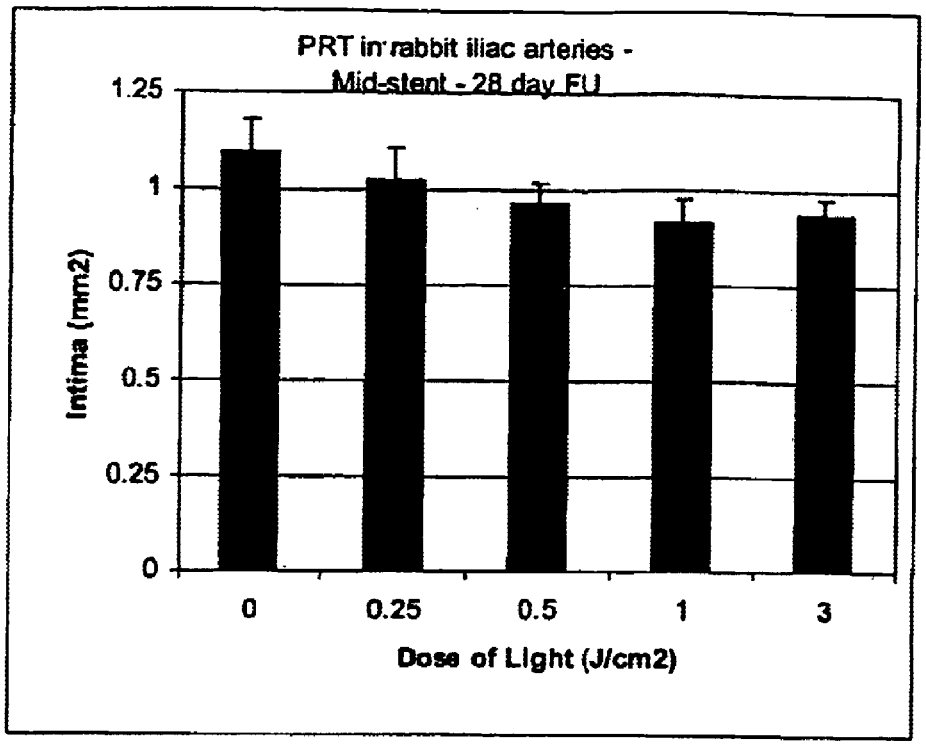
FIG. 1 is a plot of mid-stent intima area in double injured rabbit arteries treated with various doses of PDT.

The methods of the invention provide for the use of one or more photosensitizers (PS) in low dose photodynamic therapy (PDT) to prevent, treat, inhibit or reduce restenosis and/or intimal hyperplasia (IH) in blood vessels in vivo. Such methods may be readily conducted by administration of the PS, either systemically or locally followed by administration of radiation to activate the PS, at a site of IH or at risk of developing IH. Local delivery of the PS provides a high local concentration while reducing the likelihood of photosensitivity or phototoxicity, such as transient skin photosensitivity, that might follow systemic PS administration. The methods of the invention result in the decrease or prevention of restenosis and/or IH at the site of irradiation. Most preferred are embodiments of the invention for use in human subjects.

In particularly preferred embodiments of the invention, the methods are used in combination with any form of percutaneous vascular intervention, such as, but not limited to, an angioplastic procedure. As used herein, "angioplasty" or "angioplastic" generally refer to any invasive or otherwise surgical procedure that traumatizes the walls of the vasculature being treated. Typically, such procedures are conducted to treat various vascular diseases including arteriosclerosis, atherosclerosis, or the plaques associated therewith. Examples of such procedures include, but are not limited to, femoral-popliteal bypasses, femoral-tibial bypasses, aorto-iliac bypasses, coronary bypasses, percutaneous transluminal angioplasty, balloon angioplasty, laser angioplasty, treatment of transplant arteriosclerosis, directional atherectomy, and rotational atherectomy (such as with a Rotoblator™). The scope of this definition includes any manipulation that results in restenosis and/or IH, including the placement or deployment of a stent as part of, or in a procedure subsequent to, any of the above listed procedures. In humans, "angioplasty" or "angioplastic" refer to the above described procedures as used on blood vessels afflicted by pre-existing disease.

As used herein, the phrases "in combination with angioplasty" or "in combination with an angioplastic procedure" "as an adjunct to angioplasty" or "as an adjunct to an angioplastic procedure" refer to the occurrence of a protocol at a time before, simultaneous with, or after said angioplasty or angioplastic procedure. Generally, the protocol occurs as part of the same vascular intervention. In preferred embodiments of the invention, the low dose includes the administration of one or more PS immediately (such as, but not limited to, about one to about thirty or about sixty seconds, or about one to about 15 minutes) before, or simultaneous with, angioplasty. In some embodiments of the invention, the administration of PS is from about 1 minute to about two hours, more preferably from about 10 minutes to about one hour, or depending upon the mode of administration of the PS. If the PS is administered following the end of the angioplasty procedure, administration is conducted as soon as practicable, preferably from about 1 to about 10 minutes, more preferably about 1–2, about 2–3, about 3–4, about 4–5, about 5–6, about 6–7, about 7–8, about 8–9, or about 9–10 minutes, before angioplasty. Modes of the invention for such administration are further provided below. In another preferred embodiment of the invention, one or more PS is administered starting from about one to about fifteen minutes after the angioplasty. In some of these embodiments of the invention, PS administration begins from about 1–3, about 3–5, about 5–7, about 7–9, about 9–11, about 11–13, or about 13–15 minutes after angioplasty.

Simultaneous administration of PS refers to administration during an ongoing angioplasty procedure. In an additional embodiment of the invention, a single device, such as but not limited to a balloon catheter, may be used to perform the angioplastic procedure as well as administer PS and deliver radiation.

Application of radiation, containing one or more wavelengths capable of activating the administered PS and performed as part of PDT, preferably follows completed above described PS administration. In preferred embodiments of the invention, irradiation occurs immediately or shortly after completion of PS administration, in a time period of no more than about 15–30 minutes after PS administration. Even more preferred are embodiments where irradiation occurs between about one and about 10 or 15 minutes after PS administration. Such preferred embodiments include irradiation within about 1–2, about 2–3, about 3–4, about 4–5, about 5–6, about 6–7, about 7–8, about 8–9, about 9–10, about 10–11, about 11–12, about 12–13, about 13–14, or about 14–15 minutes after PS administration.

Restenosis as used herein refers to any narrowing of a blood vessel following the removal or reduction of a previous narrowing. The use of the term does not limit the present invention to any proposed underlying mechanism thought to be causally connected to restenosis. As such, restenotic lesions or sites may be the result of intimal hyperplasia and/or arterial remodeling and/or any other mechanistic cause.

Intimal hyperplasia (IH) is defined and used herein as a pathophysiological condition which may lead to the partial or complete occlusion of blood vessels if left untreated. The occlusion of vasculature resulting from IH is accompanied by cell proliferation, include that of smooth muscle cells (SMCs) in the vasculature, which may result in a stenosis (narrowing of a blood vessel). Without being bound by theory, the present invention may reduce IH at least in part by modulating the activation and/or proliferation of medial SMCs and/or adventitial myofibroblasts by means of a moderate apoptotic response and/or altering the mitogenic and stress-activated intracellular signaling pathways. The present methods may also act at least in part by modulating the behavior of, or selectively eliminating, immune cells present at locations containing IH. Regardless of whether the above are correct, the present invention is designed to affect such cell proliferation such that IH is reduced.

Additionally, the present invention induces sufficient amounts of necrosis and/or apoptosis at the site of treatment such that IH is reduced but unwanted thrombosis is not appreciably induced or stimulated. Photothrombosis has been observed to occur with the use of PDT doses higher than those of the present invention. Moreover, the present invention preferably does not extensively damage the media of the treated vasculature, deplete all endothelial and smooth muscle cells (SMCs), or result in a block to re-endothelialization. As such, the present invention preferably does not render the lumenal space or the media of a blood vessel acellular. Instead, the invention preferably inhibits restenosis while not preventing normal re-endothelialization of the blood vessel and other normal healing events. Damage to the media, including the destruction of all cells therein, depletion of all endothelial cells and SMCs, and the inhibition of re-endothelialization are likely events with the use of PDT doses higher than those of the present invention.

The low dose PDT methods of the invention may be applied at sites containing IH or at risk of developing IH. The application of PDT at such sites may occur in combination with angioplasty, and localized administration of PDT may be by any known means. In most embodiments of the invention the steps of administering PS and radiation which make up PDT are conducted within the lumen of a blood vessel. Examples of localized PS administration include, but are not limited to, direct injection within vasculature to a site of IH or the use of a drug delivery catheter (DDC) to administer the PS to said site. Exemplary embodiments of DDC include diffusion, pressure driven or mechanical design catheters. Diffusion balloon designs include double balloon, multichamber balloon (e.g. Dispatch™, SciMed), hydrogel coated balloon or PS coated stents. Pressure driven balloon designs include, but are not limited to, devices with different pore sizes such as microporous (Crescendo™, Cordis), macroporous or regular pore size balloon (Wolinsky balloon), as well as balloon in a balloon (Transport™, Endosonics), Channeled balloon (Boston Scientific), Infusion sleeve (LocaMed). Mechanical design catheters include devices such as Iontophoretic balloon (CorTrak) or Needle Catheter (BMT Ltd.). The present invention may be practiced with a large variety of commercially available catheters or balloon catheters. Preferably, balloon catheters used in the present invention are devices that contain a plurality of small holes to deliver PS locally after inflation of the catheter. Examples of such balloon catheters include those containing about 40 to several million holes ranging in size from about 25 µm to 0.1 µm, or a fraction thereof, in diameter. In diffusion balloon designs, positive pressure may also be used to increase the rate of PS administration.

Other devices for drug delivery are described in U.S. Pat. Nos. 5,458,568 and 5,232,444; and WO 9505866, 9405361 and 9211895. See also Gonshior et al. (Amer. Heart J. 130(6):1174–1181, 1995) for a comparison of catheter systems.

One or more PS may be locally administered via the above methods, whether or not a stent has been used in combination with the angioplastic procedure. If a stent is used in the angioplasty, the PS may be delivered with the introduction of the stent (see U.S. Pat. Nos. 5,419,760 and 5,429,634, for example). Alternatively, PS administration may be by the above described methods after deployment of the stent. If a stent is not deployed as part of the angioplasty, the present invention may be combined with a subsequent procedure to deploy a stent.

The deliberate application of radiation to activate the administered PS is also preferably localized to the site of, or at risk of, IH. This may occur by any means, including, but not limited to, direct irradiation of the site from a source inside or outside a blood vessel. Without limiting the invention, irradiation from inside a blood vessel may occur via the use of a catheter or fiberoptic probe, each of which may be optionally fitted with a diffuser, or a free floating fiber that is a fiber optic diffuser. Preferred embodiments for irradiation from inside the vasculature include the use of a catheter for radiation delivery and a radiation diffusing catheter. The preferred form of radiation is light energy.

Light delivery catheters preferably utilize a light permeable tip and balloon material that, when inflated, allows direct transmission of the light to the site within the vasculature. Such catheters may be of blood flow obstructing or perfusion designs. In the blood flow obstructing designs, the balloon when inflated blocks the blood vessel lumen and stops the blood flow while the balloon is inflated (for the duration of the treatment, for example). In the perfusion design, the catheter allows for continuation of the blood flow through the area that is being treated. Perfusion catheter designs include but are not limited to special geometry balloons with longitudinal channels, catheter shafts with channels for blood perfusion and undersized balloons where there is a gap between the outside diameter of the balloon and the inside diameter of the treatment area.

Light diffusing catheters are used to deliver light energy generated by an external source to the treatment site. The light diffusing catheters preferably are composed of an optical fiber (optionally of about 200 µm in core diameter) that ends distally in a cylindrical light-diffusing tip. The functions of light delivery and diffusing catheters may be optionally combined in a single catheter or a light diffusing catheter may be used alone without a centering balloon. The source of light energy is preferably capable of producing coherent light, of a single wavelength or a range of wavelengths, suitable for activation of the administered PS.

Alternatively, the radiation may be delivered externally, such as by direct irradiation of the treated vasculature or via a flexible patch diffuser that can be wrapped around a treated blood vessel. Preferably, the light source is a laser, and the light energy generated is of a wavelength and intensity sufficient to activate the PS in a short period of time, usually on the order of seconds to minutes.

The dosage of PDT is dependent on multiple factors. It is understood that the manipulation of these parameters will vary according to the nature of the blood vessel tissue being treated and the nature of the PS employed. However, and in general, low dose PDT employs combinations of factors such as the drug concentration, intensity, and total energy values which are lower than those conventionally used for destroying target tissues such as tumors and unwanted neovascularization. One measure might be the product of PS concentration (e.g., in ng/ml)×intensity (e.g., in mW/cm$^2$)×time (e.g., in seconds). However, it is difficult to set absolute numbers for this product since there are constraints on each of the parameters individually. For example, if the intensity is too low, the PS will not be activated consistently; if the intensity is too high, hyperthermic and other damaging effects may occur. Similarly, PS concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the PS employed, and in general, an increase in intensity would permit a decrease in time of irradiation, and so forth. Stated differently, the maintenance of a low dose may result in a value in the upper ranges of one factor mandating a value in the lower ranges of another factor.

The following factors are those of significant importance and susceptible to adjustment: the nature of the PS used, the amount of PS administered, the effective yield of the PS after photoactivation (generally this refers to the efficiency of PS photoactivation being converted to a PDT effect, but in the case of green porphyrins and other postulated singlet oxygen generating PS, this may also be viewed as the efficiency and yield at which an activated PS molecule generates singlet oxygen), the amount and wavelength of radiation energy administered, the degree of scatter or other interference to photoactivation of PS, and, in the case of PS that generate singlet oxygen, the amount of molecular oxygen available. Exemplary PS for use with the present invention are provided below, and the choice of a PS determines the effective yield. An "effective amount" of a PS refers to an amount suitable for low dose PDT as provided herein.

In the preferred embodiments of the invention using green porphyrins and other porphyrin derivatives in local administration as described above, the preferred concentration is in, but not limited to, the range of about 1.0 ng/ml to 2 mg/ml. More preferable are concentrations from about 0.2 to 0.5, about 0.5 to 0.75, about 0.75 to 1.0, about 1.0 to 1.25, about 1.25 to 1.5, about 1.5 to 1.75, and about 1.75 to 2 mg/ml. Other concentrations that may be used include from about 2 ng/ml–1 µg/ml, and typically in the range of 10 ng/ml–100 ng/ml. However, these values are merely suggestions and may not apply to all PSs. For localized application of BPD-MA, a range of about 0.01 to about 1.0 mg/ml is contemplated. Preferably, about 0.2 mg/ml is used.

For systemic application of PS, the range should be lower than that used for treating neovasculature, which is about 2–8 (or more preferably 6) mg/m$^2$ (BPD-MA/body surface area). Preferably, a range of less than 0.1–2 mg/m$^2$ of BPD-MA is used. Systemic administration can also be stated in terms of amount of PS to body weight of the subject being treated. Dosages for this invention stated in such terms are less than about 10 µg/kg to 100 mg/kg body weight, preferably less than 100 µg/kg to 10 mg/kg, more preferably less than about 1 mg/kg in mice and less than about 0.2 mg/kg in humans.

As an alternative to the above means of describing PS concentrations, the dosage may also be described in terms of concentration in the blood vessel walls after delivery. In preferred embodiments of the invention using green porphyrins, examples of such concentrations are in the range of, but not limited to, 0.1 ng/mg to 25 ng/mg. More preferable are concentrations from about 0.1 to 10 µg/g (or about 0.1 to 10 ng/mg) of blood vessel tissue. Even more preferred are concentrations in the range of about 0.1 to 0.5, about 0.5 to 0.75, about 0.75 to 1.0, about 1.0 to 2.0, about 2.0 to 3.0, about 3.0 to 4.0, about 4.0 to 5.0, about 5.0 to 6.0, about 6.0 to 7.0, about 7.0 to 8.0, about 8.0 to 9.0, and about 9.0 to about 10 ng/mg tissue. One non-limiting means of determining tissue concentrations of PS is via biopsy of tissue sample followed by any detection means, including, but not limited to, mass spectroscopy.

The amount and wavelength of radiation applied is dependent on the nature of the PS used and the effective yield described above. As such, the amount and wavelength should be selected accordingly based on PS selection. For example, the selection of a PS with an activation wavelength in the ultraviolet (UV) region of the electromagnetic spectrum and a low effective yield would lead to the application of UV radiation at a relatively high levels. In the preferred embodiments of the invention using green porphyrins, the choice of wavelengths is in the visible range, more preferably from about 400 to about 730 nm or from about 650 to about 730, and most preferably at about 690 nm. Irradiation with light in the blue range, such as from about 440 to about 480 nm, may also be used in the practice of the present invention.

The light dose of such radiation is typically in the range of about 0.25 to 200 $J/cm^2$, and will vary depending on the choice of PS and concentration as noted above. In preferred embodiments of the invention involving the use of green porphyrins, the light dosage is preferably from about 0.25 to about 0.5, from about 0.5 to 0.75, from about 0.75 to 1.0, from about 1 to 2, from about 2 to 5, from about 5 to 10, from about 10 to 15, from about 15 to 20, from about 20–25, from about 25 to 50, from about 50–75, from about 75 to 100, from 100 to 125, from about 125 to 150, from about 150 to 175, and from about 175 to 200 $J/cm^2$. Light dosages in the practice of the invention may be delivered at a variety of fluence rates, such as those ranging from about 10 $mW/cm^2$ to about 600 $mW/cm^2$, preferably between about 10 to about 250 $mW/cm^2$. Because the relationship between total light dosage applied and fluency is merely a factor of time (where dosage in Joules equals the fluency in Watts times seconds), the choice of fluence rates depends in part upon the duration of irradiation. For example, a dosage of 0.25 $J/cm^2$ may be applied at a fluency of 50 $mW/cm^2$ for 5 seconds or a fluency of 25 $mW/cm^2$ for 10 seconds.

As for the potential scatter of the applied radiation, the use of catheters and balloon catheters as described above function to minimize the degree of interference with PS activation. Without limiting the invention, and provided for the purpose of improving the understanding of thereof, it should be noted that a small amount of scatter may be advantageous in certain embodiments of the invention. For example, embodiments of the invention that involve PDT after deployment of a stent derived an advantage from the scatter of radiation from vascular cells that are directly irradiated (not blocked from radiation by the physical material of the stent) to cells not directly irradiated (due to blockage by the stent). Similarly, the material of the stent may be such that it scatters light and permits it to reach cells that would otherwise be blocked by the stent from irradiation.

In preferred embodiments of the invention using green porphyrins, porphyrin derivatives, or other singlet oxygen generating PS, the amount of available molecular oxygen may be a limiting factor in the PDT methods of the invention. This is of particular relevance in embodiments of the invention wherein a balloon catheter is inflated, thus blocking bloodflow and its associated delivery of oxygen, and then used to apply radiation to the site of PDT. While normal blood vessels have access to oxygen supplied by the vasa vasorum—a vascular plexus that drains the adventitia and the media—and the lumen, in thin arteries, balloon dilation and stenting are likely to compact the vasa vasorum and decrease or limit the oxygen supply. Such compaction may also occur in embodiments of the invention where the light delivery catheter is flushed with the vessel wall. These considerations suggest the possibility of a shortage of the oxygen supply during PDT.

The present invention also takes into account results suggesting that in rabbit arteries, the response of the vessel to PDT appears to plateau after a light dose of 0.25 $J/cm^2$, which suggests that there is a limiting factor. Because light is not the limiting step and the amount of PS used was sufficiently high, oxygen tension (or availability) in the treated artery is likely to be the limiting factor.

As such, the present invention may also be practiced with the use of fractionated delivery of radiation wherein a total dose of radiation is delivered in fractions by a balloon catheter that is inflated and deflated a number of times to permit partial delivery of the radiation after each inflation and partial or complete restoration of oxygen delivery after each deflation. In preferred embodiments of the invention, fractionated delivery divides the total radiation dose into from about 2 to about 10 cycles of inflation/deflation. More preferred are the use of from about 2 to 4, about 4 to 6, about 6 to 8, or about 8 to 10 cycles to deliver radiation.

In another embodiment of the invention, oxygen supply to the target site is maintained by use of a free floating fiber optic to deliver light or a perfusion balloon that allows for blood flow in the lumen during light delivery. In such instances, the perfusion balloon can be an undersized membrane (outside diameter of the membrane is smaller than the inside diameter of the vessel in the treatment area) or a balloon with longitudinal channels (star shape in cross section) to allow blood to flow along the vessel wall during treatment. Such light delivery devices may also be used to deliver radiation in a single, non-fractionated manner. A free floating fiber optic may be introduced along a guide wire used for angioplasty and/or PS delivery.

As noted above, the present invention relates to inhibiting or reducing restenosis, especially that which accompanies angioplastic procedures and results in a decrease in the mean luminal diameter of a blood vessel when compared to the mean luminal diameter immediately after angioplasty. Thus the degree of inhibition or reduction of restenosis may also be viewed in terms of a reduction in the mean luminal diameter loss caused by the restenosis as compared to the loss in blood vessels untreated by any anti-restenotic therapy or blood vessels treated by alternate means of anti-restenotic therapy. Stated differently, the mean luminal diameter loss due to restenosis may be reduced by use of the present invention. Preferably, the mean luminal diameter loss is reduced by at least 10%, more preferably at least 20, 30, 40, 50, 60, 70, 80, or 90%. Most preferred is a reduction of up to 100%. Such reductions in mean luminal diameter loss may be determined by measurements conducted at a time point 6 months post angioplasty. Alternatively the measurements may be taken at an earlier time point, including one, two, three, four, or five months post angioplasty.

The above reduction in mean luminal diameter loss may also be described as a larger mean luminal diameter that results from the use of the present invention, as compared to the mean luminal diameter in blood vessels untreated by any anti-restenotic therapy or blood vessels treated by alternate means of anti-restenotic therapy. Preferably, the mean luminal diameter is increased by at least 10%, more preferably at least 20, 30, 40, 50, 60, 70, 80, or 90%. In additional embodiments of the invention, the mean luminal diameter may be increased by about 100% or more, up to a diameter that reflects the absence of restenosis.

PHOTOSENSITIZERS AND PRT

Photosensitizers (PS) suitable for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl) selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a;

bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo[3,2-g] [1] benzopyran-2-one; 2H-selenolo[3,2-g] [1] benzothiopyran-2-one; 7H-selenolo[3,2-g] [1] benzoseleno-pyran-7-one; 7H-selenopyrano[3,2-f] [1] benzofuran-7-one; 7H-selenopyrano[3,2-f] [1] benzothiophene-7-one; 2H-thienol[3,2-g] [1] benzopyran-2-one; 7H-thienol[3,2-g] [1] benzothiopyran-7-one; 7H-thiopyrano[3,2-f] [1] benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra-(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2'"3'"-q) porphyrazine; zinc (II) 2-(3-pyridyloxy)benzo[b]-10,19,28-tri(1,1-dimethylethyl)trinaphtho[2',3'-g:2"3"1::2'",3'"-q] porphyrazine; zinc (II) 2,18-bis-(3-pyridyloxy)dibenzo[b,1]-10,26-di(1,1-dimethyl-ethyl)dinaphtho[2',3'-g:2'",3'"-q] porphyrazine; zinc (II) 2,9-bis-(3-pyridyloxy)dibenzo[b,g]-17,26-di(1,1-dimethyl-ethyl)dinaphtho[2",3"-1:2'",3'"-q] porphyrazine; zinc (II) 2,9,16-tris-(3-pyridyloxy) tribenzo[b,g,1]-24=(1,1-dimethyl-ethyl)naphtho[2'",3'"-q] porphyrazine; zinc (II) 2,3-bis-(3-pyridyloxy) benzo[b]-10,19,28-tri(1,1-dimethyl-ethyl)trinaphtho[2',3'-g:2",3"1:2'", 3'"-q]porphyrazine; zinc (II) 2,3,18,19-tetrakis-(3-pyridyloxy) dibenzo[b,1]-10,26-di(1,1-dimethyl-ethyl) trinaphtho[2',3'-g:2"',3'"-q]porphyrazine; zinc (II) 2,3,9,10-tetrakis-(3-pyridyloxy) dibenzo[b,g]-17,26-di(1,1-dimethyl-ethyl)dinaphtho[2',3'-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[2'",3'"-q]porphyrazine; zinc (II) 2-(3-N-methyl)pyridyloxy)benzo[b]-10,19,28-tri(1,1-dimethyl-ethyl)trinaphtho[2',3'-g:2',3'1:2'", 3'"-q] porphyrazine monoiodide; zinc (II) 2,18-bis-(3-(N-methyl) pyridyloxy)dibenzo[b,1]-10,26-di(1,1-dimethylethyl) dinaphtho[2',3'-g:2'",3'"-q]porphyrazine diiodide; zinc (II) 2,9-bis-(3-(N-methyl)pyridyloxy)dibenzo[b,g]-17,26-di(1,1-dimethylethyl)dinaphtho[2',3'-1:2'",3'"-q]porphyrazine diiodide; zinc (II) 2,9,16-tris-(3-(N-methyl-pyridyloxy) tribenzo[b,g,1]-24-(1,1-dimethylethyl)naphtho[2'",3'"-q] porphyrazine triiodide; zinc (II) 2,3-bis-(3-(N-methyl) pyridyloxy)benzo[b]-10,19,28-tri(1,1-dimethylethyl) trinaphtho[2',3'-g:2',3'-1:2'",3'"-q]porphyrazine diiodide; zinc (II) 2,3,18,19-tetrakis-(3-(N-methyl)pyridyloxy) dibenzo[b,1]-10,26-di(1,1-dimethyl)dinaphtho[2',3'-g:2'", 3'"-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2',3'-1:2'",3'"-q]porphyrazine tetraiodide; zinc (II) 2,3,9,10,16,17-hexakis-(3-(N-methyl)pyridyloxy)tribenzo[b,g,1]-24-(1,1-dimethylethyl)naphtho [2'",3'"-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfophthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminun phthalocyanine disulfonate; aluminum phthalocyanine disulfonate (cis isomer); aluminum phthalocyanine disulfonate (clinical prep.); aluminum phthalocyanine phthalimidomethyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethylamino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; GaPcS$_1$tBu$_3$; GaPcS$_2$tBu$_2$; GaPcS$_3$tBu$_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; HOSiPcOSi(CH$_3$)$_2$(CH$_2$)$_3$N(CH$_3$)$_2$; HOSiPcOSi(CH$_3$)$_2$(CH$_2$)$_3$N(CH$_2$CH$_3$)$_2$; SiPc[OSi(CH$_3$)$_2$(CH$_2$)$_3$N(CH$_3$)$_2$]$_2$; SiPc[OSi(CH$_3$)$_2$(CH$_2$)$_3$N(CH$_2$CH$_3$)(CH$_2$)$_2$N(CH$_3$)$_2$]$_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy) phthalocyanine complex octaiodide; and zinc (II) 2,3,9,10,16,17,23,24-octakis-(3-pynridyloxy)phthalocyanine.

Exemplary methylene blue derivatives include 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxaziniun, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy isohypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)] hypocrellin B; 5,8-dibromo[1,12-CHBrC(=CH$_2$)CBr(COMe)] hypocrellin B; 5,8-dibromo[1-CH$_2$COMe, 12-COCOCH$_2$Br-] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)-] hypocrellin B; 5,8-diiodo[1,12-CH$_2$C(CH$_2$I)=C(COMe)-] hypocrellin B; 2-(N,N-diethylamino) ethylaminated hypocrellin B; 3,10-bis[2-(N,N-diethylamino)-ethylamine]hypocrellin B; 4,9-bis[2-(N,N- diethyl-amino)-ethylamine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-$CH_2C(CH_2I)$=C(COMe)-] hypocrellin B; 8-iodo[1,12-$CH_2C(CH_2I)$=C(COMe)-] hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl $13^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl) bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl) bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9(N-t-butoxycarbonylglycinoxy) porphycene; 2,7,12,17-tetrakis(2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)porphycene; 2,7,12,17-tetrakis(2-methoxyethyl)-9-(glutarimido)-porphycene; 2,7,12,17-tetrakis(2-methoxyethyl)-3-N,N-dimethylaminomethyl)-porphycene; 2,7,12,17-tetrakis(2-methoxyethyl)-3-N,N-dimethylaminomethyl)-porphycene hydrochloride; 2,7,12,17-tetrakis(2-ethoxyethyl) porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6; 13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin, deuteroporphyrin IX dimethylester; diformyldeuteroporphyrin IX dimethylester; dodecaphenylporphyrin; hematoporphyriri; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphynrn IX dimethylester; monoforrnyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra (4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl) porphine; meso-tetra(4-sulfonatophenyl)porphine; tetrakis (4-sulfonatophenyl)porphyrin; meso-tetra(4-N-trimethylanilinium)-porphine; uroporphyrin; uroporphyrin 1 (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodarnine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophenc-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'",1'"-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3'",3'"-dimethylacryloyloxyrnethyl)-2,2':5',2"-terthiophene; 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonarnide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2, 2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',2":5",2'''-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester, and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion)p-isopropylbenzyl ester, eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phioxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammoniun salt; rose bengal ethyl ester; rose bengal methyl ester; rose bengal octyl ester tri-n-butyl-ammonium salt RB; rose bengal, 6'-O-acetyl-, and ethyl ester.

Also suitable for the practice of the invention are the class of PS referred to as "green porphyrins." A "green porphyrin" (Gp) is a porphyrin derivative obtained by reacting a porphyrin nucleus with an alkyne in a Diels-Alder type reaction to obtain a mono-hydrobenzoporphyrin. Such resultant macropyrrolic compounds are called benzoporphyrin derivatives (BPDs), which is a synthetic chlorin-like porphyrin with various structural analogues, as shown in U.S. Pat. Nos. 5,283,255, 4,920,143, 4,883,790, and 5,171,749, all of which are hereby incorporated in their entireties as if fully set forth. Non-limiting examples of green porphyrin derivatives are also discussed in U.S. Pat. No. 5,880,145 and related U.S. patent application Ser. No. 09/265,245, both of which are hereby incorporated in their entireties as if fully set forth.

Typically, green porphyrins are selected from a group of tetrapyrrolic porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B). Metallated forms of a Gp, in which a metal cation replaces one or two hydrogens in the center of the ring system, may also be used in the practice of the invention. The preparation of the green porphyrin compounds useful in this invention is described in detail in U.S. Pat. No. 5,095,030, which is hereby incorporated by reference as if fully set forth.

Preferably, the BPD is a benzoporphyrin derivative di-acid (BPD-DA), mono-acid ring A (BPD-MA), mono-acid ring B (BPD-MB), or mixtures thereof. These compounds absorb light at about 692 nm wavelength and have improved tissue penetration properties. The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. A number of other BPD B-ring derivatives may also be used in the present methods (see FIG. 3 and the following Tables 1 and 2).

TABLE 1

| 4.1 DRUG | X1 | X2 | X3 |
|---|---|---|---|
| QLT0061 | COOH | COOH | COOH |
| QLT0077 | $CONH(CH_2)_2N^+(CH_3)_3I^-$ | $CONH(CH_2)_2N^+(CH_3)_3I^-$ | $COOCH_3$ |
| QLT0079 | $CONH(CH_2)_2N^+(CH_3)_2((CH_2)_3CH_3)$ | $CONH(CH_2)_2N^+(CH_3)_2((CH_2)_3CH_3)$ | $COOCH_3$ |
| QLT0086[1] | $CONHCH(COOH)CH_2COOH$ | $CONHCH(COOH)CH_2COOH$ | $COOCH_3$ |
| QLT0092[2] | $CONH(CH_2)_2NH(CH_3)_2$ $CF_3COO^-$ | $CONH(CH_2)_2NH(CH_3)_2$ $CF_3COO^-$ | $COOCH_3$ |
| QLT0094 | $CONHCH_2COOH$ | $CONHCH_2COOH$ | $CONHCH_2COOH$ |

[1]Batch contains trace amounts of $CF_3COO^-$.
[2]Batch contains 4 × ($CF_3COO^-$).

TABLE 2
Lipophilic BPD B-ring analogs

| Drug | X1 | X2 | X3 |
|---|---|---|---|
| QLT0060 | $CO(O(CH_2)_2)OH$ | $CO(O(CH_2)_2)OH$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Particularly preferred PSs are BPD-MA, EA6, and B3. Of course, combinations of PS may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

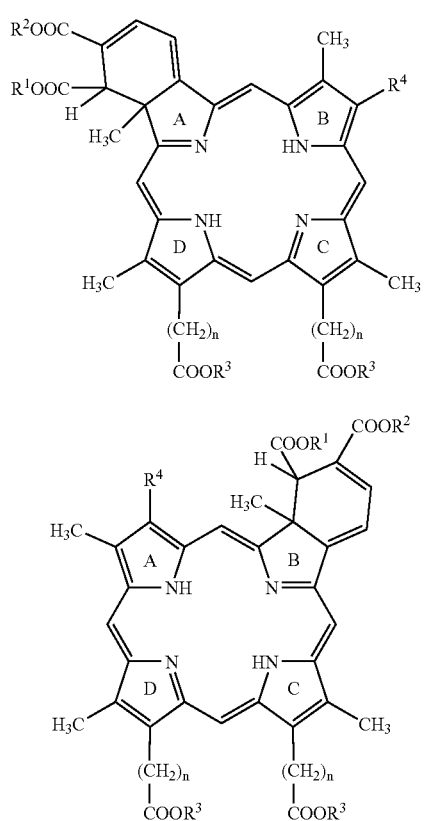

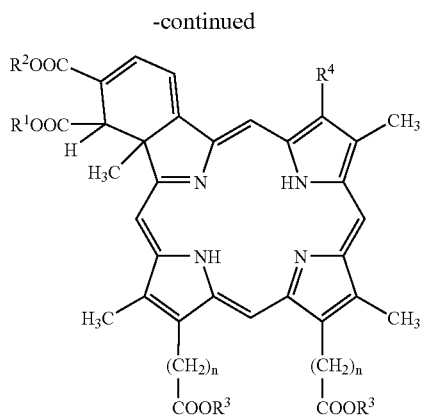

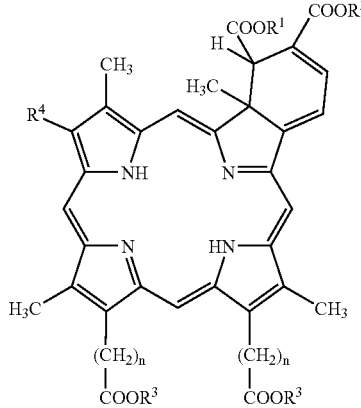

where $R^4$ is vinyl or 1-hydroxyethyl and $R^1$, $R^2$, and $R^3$ are H or alkyl or substituted alkyl.

BPD-MA has the structure shown in FIG. 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin™, as well as illustrations of A and B ring forms of EA6 and B3, are as follows:

BPD-MA<sub>C</sub>

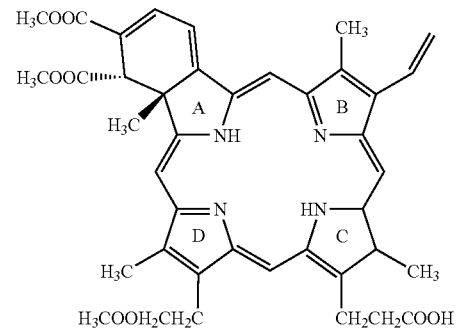

BPD-MA<sub>D</sub>

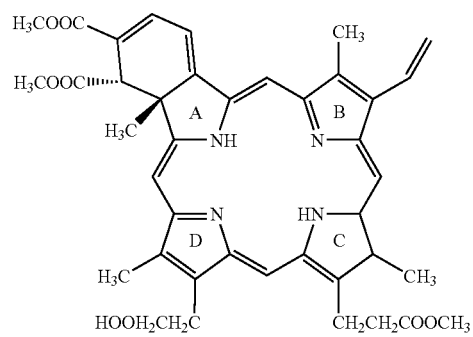

A-EA6

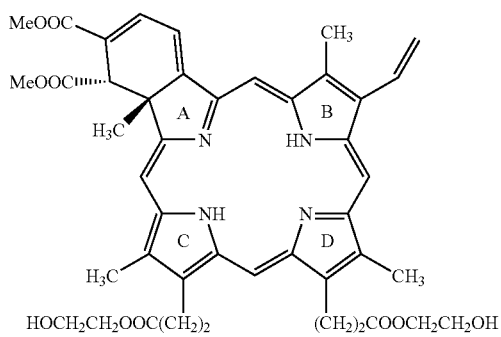

B-EA6

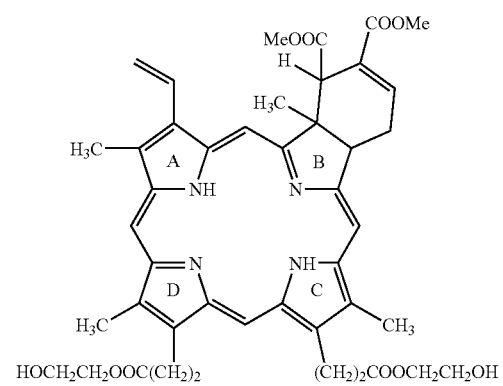

A-B3

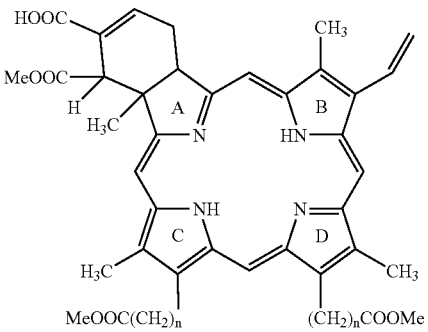

B-B3

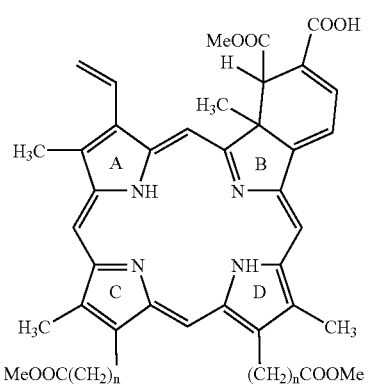

Related compounds of formulas 3 and 4 are also useful; in general, $R^4$ will be vinyl or 1-hydroxyethyl and $R^1$, $R^2$, and $R^3$ are H or alkyl or substituted alkyl.

Used as part of the present invention, some PS, such as phthalocyanines, may be used in higher concentrations sufficient to offset their relatively slower uptake by cells of a blood vessel. An optimal PS for use in the present invention should be rapidly taken up by cells in the intima and media of blood vessels.

A particularly preferred PS according to the present invention will satisfy the following general criteria: 1) it is capable of rapid entry into the cells of blood vessel intima and media; and 2) irradiation of the, preferably with light, results in the inhibition or reduction of restenosis.

After PS administration, sufficient time is permitted to elapse for the PS to be taken up by the cells of the blood vessel wall. This time for uptake may be varied according to various parameters, including but not limited to the photosensitizer administered, the route of administration, the physiology of the subject and of the vessel wall cells, and the artisan's skill and experience. With green porphyrins, for example, the elapsed time may be from less than about one minute to more than thirty minutes. The cells, or tissues containing them, are then irradiated at the wavelength of maximum absorbence, or any other excitation wavelength, of the PS. In the case of BPDs, the wavelength is usually between about 550 and 695 nm, as discussed above. In particular, red light is advantageous because of its relatively lower energy and the resulting lack of toxicity it poses to normal tissue.

In addition to the radiation delivery systems discussed above, and for embodiments of the invention involving visible light radiation, irradiation may be performed by sources such as, but not limited to, operating room lamps, halogen lamps, fluorescent lamps, laser light sources, and combinations thereof. Additional examples of light sources include light emitting diode (LED) panels or flexible light diffusers which may be wrapped around a blood vessel. With such sources, the exterior (adventitia) of a BPD-MA treated blood vessel is exposed to light. This is in contrast to intraluminal irradiation methods which may also be used in combination with the present invention.

The PS for use in the present invention are optionally formulated with additional components. Preferred additionally components include, but are not limited to, those that increase the efficacy,. delivery, stability or other advantageous characteristic of the PS for use in the present invention. The formulation may be a liposomal formulation, or other lipid or phospholipid based formulation, an emulsion, or simply an aqueous solution. Buffers and other excipients may also be added. Gelling agents and other excipients may also be employed.

Particularly preferred formulations are those suitable for administration into a blood vessel, such as sterile, buffered, apyrogenic, and/or isotonic formulations.

KITS

The present invention also provides kits that incorporate the features of the invention and makes possible a convenient means of practicing the invention. Kits of the invention comprise one or more PS as described above and may also include other materials that facilitate the practice of the invention, such as, but not limited to, a catheter. The items comprising the kit may be supplied in the form of individual packages and/or packaged together, as desired by the skilled person.

In one embodiment, a kit comprises at least one PS in a suitable container. Preferably, the kit contains at least an indication, such as, but not limited to, packaging or a label, identifying the kit or the PS as suitable for use in the applications described herein for the present invention and/ or at least one instruction relating to the use of the kit or the PS in the applications described herein for the present invention. Optionally, the at least one instruction may be part of a larger set of instructions relating to the use of the kit or the PS in the applications described herein for the present invention or relating to the use of the kit or PS in the practice of the present invention. Even more preferred are such kits indicated as suitable for use in humans by way the packaging, label, or instructions.

The at least one PS in a kit of the invention may be provided in any form, but preferably, they are provided in a form suitable for immediate use or in a form suitable for use upon reconstitution. As such, the at least one PS may be provided in a small volume (e.g. about 100 ml to about 1.0 ml in size) in a suitable formulation as described above or in a suitable formulation for reconstitution (e.g. with sterile water or pyrogen free water or injectable buffer solutions.

The following examples are intended to illustrate but not to limit the invention.

EXAMPLE 1

Materials and Methods Used

Verteporfin for Injection™ was used with a porous balloon drug delivery catheter. This device is an rapid exchange perfusion catheter that utilizes a 20 mm long balloon containing 40—25 um diameter holes used to deliver the compound locally into a vessel. The light delivery catheter used is an OTW catheter, with a 20 mm long balloon, that utilizes a light permeable tip and balloon material that when inflated allows the light energy to be directly transmitted to the vessel. A light diffusing catheter was also used. This device is a 200 μm optical fiber that ends distally in a cylindrical light-diffusing tip. The light energy generated by an external laser is delivered to the treatment site through the diffusing catheter. The diffusing section of the catheter is 20 mm in length.

The stent used (S670) is balloon expandable stent made up of discrete 1.5 mm zigzag segments. The S670 stents are compressed and mounted onto the balloon portion of a catheter delivery system. The stents used in this study were be 12 mm in length. The laser light source was a Coherent OPDL Photoactivator 689 +/−3 nm, 200 mW There were five treatment factors:

T0: Stent Injury, Placebo Delivery, Light Delivery Balloon (no photons)

T1: Stent Injury, Verteporfin for Injection™ Delivery of 0.36 mL to the target tissue (1.15 mL total volume) at 0.2 mg/mL concentration, Light Delivery Balloon (0.25 J/cm2)

T2: Stent Injury, Verteporfin for Injection™ Delivery of 0.36 mL to the target tissue (1.15 mL total volume) at 0.2 mg/mL concentration, Light Delivery Balloon (0.50 J/cm2)

T3: Stent Injury, Verteporfin for Injection™ Delivery of 0.36 mL to the target tissue (1.15 mL total volume) at 0.2 mg/mL concentration, Light Delivery Balloon (1.0 J/cm2)

T4: Stent Injury, Verteporfin for Injection™ Delivery of 0.36 mL to the target tissue (1.15 mL total volume) at 0.2 mg/mL concentration, Light Delivery Balloon (3.0 J/cm2)

The total drug volume of 1.15 mL includes the 0.36 mL that will be delivered to the target tissue and an additional 0.79 mL of drug that is needed to fill the drug delivery catheter and will remain in catheter after delivery.

Animals were be monitored and observed at least 7 days prior to experimental use. The animals were weighed on the date of injury and again on the date of stent implantation to assure appropriate drug dosing. Animals received aspirin in drinking water (~5 mg/kg/day) starting at least one day prior to injury and continuing for the duration of the experiment.

Both iliac arteries were injured by endothelial denudation. The femoral arteries were exposed by cutdown, and are ligated distally. An arteriotomy was created in each vessel, and an angiocatheter was inserted. Nitroglycerin (20 mcg) was injected via the femoral arteriotomy to relieve vasospasm. Then, angiography was performed via injection of non-ionic contrast into the femoral arteriotomy (~4 cc) with simultaneous radiographic imaging. The angiocatheter was removed, and a 3 F Fogarty balloon was passed retrograde into the aorta via each arteriotomy. The endothelium was then denuded by withdrawing the catheter in its inflated state (0.5 cc air) three times. The femoral arteries were then ligated proximal to the arteriotomy, and the incisions were closed. The animals were subsequently be monitored according to protocol.

The photosensitizer compound, Verteporfin for Injection, was reconstituted by adding 7.0 ml of sterile water into the vial and mix gently (swirl, do not shake) for 10 seconds or until all solids dissolved. Dilution was one part of Verterporfin for Injection™ with 9 parts of 5% dextrose in water to achieve required concentration.

Reconstituted Verteporfin for Injection™ at room temperature must be used within 4 hours. Reconstituted Verteporfin for Injection™ refrigerated at 2–8° C. must be used within 14 days. Diluted Verteporfin for Injection™ must be used only on the day of dilution. Leftover diluted Verteporfin for Injection™ and leftover reconstituted Verteporfin for Injection™ will be frozen at −20° C. or below.

Approximately two weeks following the vascular injury, a stent was implanted in each iliac artery followed by PDT. Vascular access was obtained via a carotid artery, and catheters were directed under fluoroscopic guidance. The carotid artery was exposed via cutdown, ligated distally, and an arteriotomy was created. The animal received a bolus of standard heparin (100 u/kg IV) to reduce the likelihood of stent thrombosis. A 4 F Cordis sheath was inserted via the arteriotomy, permitting intra-arterial injection of nitroglycerin (20 mcg bolus, to relieve vasospasm) and angiography as detailed above. The angiographic images were reviewed, and the anatomy and sizing of the iliac arteries were determined. A stent (S670) mounted on an angioplasty balloon (3.0×12 mm, sized to assure a 1.1–1.2:1 balloon:artery diameter ratio) was then be inserted via the Cordis sheath and was directed over a wire down the aorta to one iliac artery. The stent was positioned such that its distal end is just proximal to the inguinal ligament, and will be deployed at 8 atm for 15 seconds. This process was then be repeated for the contralateral vessel.

Following stent implantation, the drug delivery catheter was positioned at the treatment site so that the balloon markers were proximal and distal to the stent. Verteporfin for Injection was then delivered at 4 atm. The drug delivery device was removed and the light delivery catheter was positioned at the treatment site (balloon markers proximal and distal to the stent). The guide wire was then removed and a light diffusing catheter positioned within the light delivery catheter. The time between drug delivery and light delivery was controlled to be within 10–15 minutes. The balloon was inflated with saline at 6 atm for the appropriate time while delivering the required amount of power. There was one control group that received a stent follow by the introduction of both the drug and light delivery devices, but with no Verteporfin for Injection or photons. Contrast injections were used to confirm device placements. There were four treatment groups that will be stented first followed by the local delivery of Verteporfin for Injection and 0.25, 0.50, 1.0 or 3.0 J/cm2 of 689 nm light.

The endpoints of this study examined the vessel patency and intimal reaction of the treated vessels. Twenty-eight days after the second procedure, the animals were euthanized with a lethal injection of intravenous Nembutal. After systemic perfusion with Ringer's Lactate and 4% paraformaldehyde, the treated iliac segments were removed in their entirety, proximal and distal ends identified and marked, and fixed in 4% paraformaldehyde. Complete histopathological analysis was performed on the vessels.

EXAMPLE 2

Rabbit Double Injury Model

Figure 2:
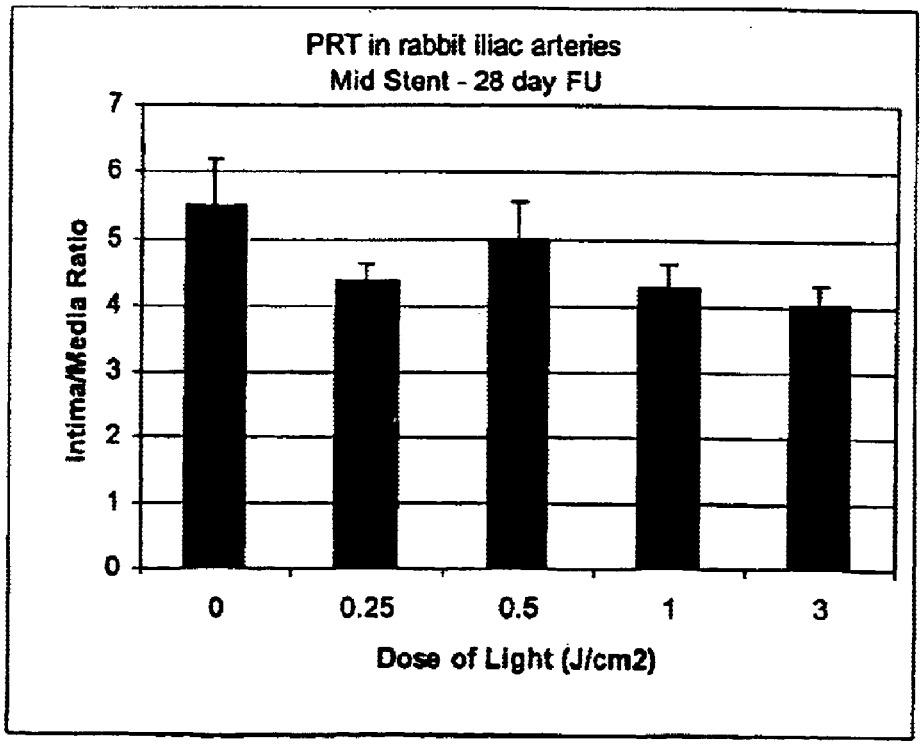
FIG. 2 is a plot of mid-stent intima to media area ratios in double injured rabbit arteries treated with various doses of PDT.

The following are the results from the above described experiments, which are also shown in FIGS. 1 and 2.

| Dose (J/cm2) | 0 | 0.25 | 0.5 | 1 | 3 |
|---|---|---|---|---|---|
| Intima | 1.093 | 1.021 | 0.966 | 0.919 | 0.942 |
| SEM | 0.087 | 0.087 | 0.049 | 0.058 | 0.035 |
| Dose (J/cm2) | 0 | 0.25 | 0.5 | 1 | 3 |
| Intima/Media | 5.503 | 4.373 | 4.979 | 4.278 | 4.03 |
| SEM | 0.706 | 0.265 | 0.574 | 0.368 | 0.286 |

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method to treat, inhibit, or reduce restenosis or intimal hyperplasia in adjunct with angioplasty in a human subject, which method comprises locally administering an effective amount of a photosensitizer to a blood vessel site that has undergone angioplasty, wherein said photosensitizer is a green porphyrin, and irradiating said site with radiation containing one or more wavelength(s) absorbed by said photosensitizer for a time and at an intensity totaling from about 0.25 to about 25 J/cm$^2$ to treat, inhibit, or reduce restenosis or intimal hyperplasia at said site without depleting all endothelial and smooth muscle cells.

2. The method of claim 1 wherein the green porphyrin is BPD-MA or A-EA6.

3. The method of claim 2 wherein said administering and irradiating steps are performed simultaneously.

4. The method of claim 2 wherein said administering step occurs within 15 minutes of said angioplasty.

5. The method of claim 4 wherein said administering step occurs within 10 minutes of said angioplasty.

6. The method of claim 2 wherein said angioplasty comprises introduction of a stent.

7. The method of claim 2 wherein said irradiating step occurs within 15 minutes of the administering step.

8. The method of claim 7 wherein said irradiating step occurs within 5 minutes of the administering step.

9. The method of claim 1 wherein said administering and irradiating steps are performed simultaneously.

10. The method of claim 1 wherein said administering step occurs within 15 minutes of said angioplasty.

11. The method of claim 10 wherein said administering step occurs within 10 minutes of said angioplasty.

12. The method of claim 1 wherein said angioplasty comprises introduction of a stent.

13. The method of claim 1 wherein said irradiating step occurs within 15 minutes of the administering step.

14. The method of claim 13 wherein said irradiatin step occurs within 5 minutes of the administering step.

* * * * *